United States Patent
Wakabayashi et al.

(10) Patent No.: US 9,439,576 B2
(45) Date of Patent: Sep. 13, 2016

(54) LIFESAVING SUPPORT APPARATUS AND LIFESAVING SUPPORT SYSTEM

(71) Applicants: NIHON KOHDEN CORPORATION, Tokyo (JP); KYOTO UNIVERSITY, Kyoto (JP)

(72) Inventors: Tsutomu Wakabayashi, Tokyo (JP); Hiroyuki Satake, Tokyo (JP); Taku Iwami, Kyoto (JP)

(73) Assignees: NIHON KOHDEN CORPORATION, Tokyo (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/132,927

(22) Filed: Dec. 18, 2013

(65) Prior Publication Data

US 2014/0180045 A1    Jun. 26, 2014

(30) Foreign Application Priority Data

Dec. 26, 2012 (JP) ................. 2012-282897

(51) Int. Cl.
| | |
|---|---|
| A61B 5/02 | (2006.01) |
| A61B 5/026 | (2006.01) |
| A61B 5/0265 | (2006.01) |
| A61B 5/1455 | (2006.01) |
| A61B 8/06 | (2006.01) |
| A61N 1/39 | (2006.01) |
| A61B 5/024 | (2006.01) |

(52) U.S. Cl.
CPC ............ *A61B 5/026* (2013.01); *A61B 5/0261* (2013.01); *A61B 5/0265* (2013.01); *A61B 5/02416* (2013.01); *A61B 5/14551* (2013.01); *A61B 8/06* (2013.01); *A61N 1/3931* (2013.01); *A61N 1/3968* (2013.01); *A61N 1/3993* (2013.01)

(58) Field of Classification Search
CPC ..................................................... A61N 1/3993
USPC ............................................................ 607/6
See application file for complete search history.

(56) References Cited

U.S. PATENT DOCUMENTS

| | | | |
|---|---|---|---|
| 2003/0120311 A1 | 6/2003 | Hansen | |
| 2004/0116969 A1* | 6/2004 | Owen et al. | ...................... 607/6 |
| 2006/0142809 A1 | 6/2006 | Kroll et al. | |

(Continued)

FOREIGN PATENT DOCUMENTS

| | | |
|---|---|---|
| EP | 1 057 498 A2 | 12/2000 |
| EP | 1 818 011 A2 | 8/2007 |

(Continued)

OTHER PUBLICATIONS

The extended European Search Report for the related European Patent Application No. 13198524.4 dated Apr. 16, 2014.

(Continued)

*Primary Examiner* — Paula J Stice
(74) *Attorney, Agent, or Firm* — Kenealy Vaidya LLP (57) ABSTRACT

A lifesaving support apparatus includes: a sensor section which is adapted to be attachable to a patient, and which is configured to acquire information of blood flow of the patient; a determining section which, based on the information of blood flow, is configured to determine whether or not a use of an automatic external defibrillator is necessary; and an outputting section which is configured to notify a rescuer of information which is determined by the determining section.

12 Claims, 4 Drawing Sheets

(56) References Cited

U.S. PATENT DOCUMENTS

| | | |
|---|---|---|
| 2006/0200203 A1 | 9/2006 | Hamilton et al. |
| 2006/0247549 A1 | 11/2006 | Chan |
| 2009/0306525 A1 | 12/2009 | Pinter et al. |
| 2010/0324615 A1 | 12/2010 | Powers |
| 2014/0052202 A1* | 2/2014 | Daynes .............................. 607/5 |

FOREIGN PATENT DOCUMENTS

| | | |
|---|---|---|
| JP | 2001-405 A | 1/2001 |
| JP | 2012-61361 A | 3/2012 |
| JP | 2012-235874 A | 12/2012 |
| WO | 2007/010422 A2 | 1/2007 |
| WO | 2009/069037 A2 | 6/2009 |
| WO | 2009/138902 A1 | 11/2009 |

OTHER PUBLICATIONS

European Office Action for the related European Patent Application No. 13 198 524.4 dated Jun. 3, 2016.

Japanese Office Action for the related Japanese Patent Application No. 2012-282897 dated Jul. 19, 2016.

* cited by examiner

LIFESAVING SUPPORT APPARATUS AND LIFESAVING SUPPORT SYSTEM

CROSS-REFERENCE TO RELATED APPLICATION(S)

This application is based upon and claims the benefit of priority from prior Japanese patent application No. 2012-282897 filed on Dec. 26, 2012, the entire contents of which are incorporated herein by reference.

BACKGROUND

The presently disclosed subject matter relates to a lifesaving support apparatus which determines whether it is necessary or not to use an automatic external defibrillator (AED), and also to a lifesaving support system which includes at least the lifesaving support apparatus and an AED.

An AED is an apparatus which applies an electric shock to a patient from whom a fatal arrhythmia such as ventricular fibrillation or pulseless ventricular tachycardia is detected, thereby resuscitating the patient. In the case where the patient is unconscious and apneic, specifically, electrode pads of the AED are applied to the chest of the denuded patient. The AED analyzes an electrocardiogram which is acquired through the electrode pads, to detect the fatal arrhythmia (for example, see JP-A-2012-61361).

In the case where an ordinary person who is not a medical person is in front of a lying patient, although the person can bring an AED, but it is usual that the person hesitates to use the AED. Even though in a cardiopulmonary arrest state, particularly, a patient in agonal stage takes a characteristic breath or a gasping breath. Therefore, it is difficult to correctly determine that the patient is unconscious and apneic. As a result, the application of an electric shock may be sometimes delayed, and this is a cause for reduction of the lifesaving rate.

Unconscious patients include those due to a brain disorder, hypoglycemia, hemorrhagic shock, near drowning, carbon monoxide poisoning, and the like. Although it is not necessary to use an AED in such patients, but it is difficult for an ordinary person to correctly determine whether the use of an AED is necessary or not. Therefore, there is a case where the privacy of the patient is not sufficiently protected, such as that where the chest is unnecessarily denuded in public. Moreover, the necessity of denuding the chest is a cause of hesitation in using an AED.

SUMMARY

The presently disclosed subject matter may provide a technique in which it is adequately determined whether a use of an AED is necessary or not, whereby a rescuer who hesitates to use an AED is supported so that the lifesaving rate is improved and the privacy of the patient can be protected.

According to as aspect of the presently disclosed subject matter, a lifesaving support apparatus may comprise: a sensor section which is adapted to be attachable to a patient, and which is configured to acquire information of blood flow of the patient; a determining section which, based on the information of blood flow, is configured to determine whether or not a use of an automatic external defibrillator is necessary; and an outputting section which is configured to notify a rescuer of information which is determined by the determining section.

The sensor section may include at least a part of a pulse oximeter.

The sensor section may include at least a part of a measuring instrument which is configured to use one of an ultrasonic wave, an electromagnetic wave, and a laser beam.

The outputting section may be configured to output the information of blood flow which is acquired by the sensor section.

The outputting section may be configured to output the information of blood flow to the automatic external defibrillator.

The lifesaving support apparatus may further comprise: a carrying-out detecting section which is configured to detect carrying out of the lifesaving support apparatus from a box in which the lifesaving support apparatus is housed together with the automatic external defibrillator; and a controlling section which, when the detecting section detects the carrying out, is configured to execute an activating process of the lifesaving support apparatus.

The lifesaving support apparatus may further comprise: an activation detecting section which is configured to detect that the automatic external defibrillator is activated; and a controlling section which, when the activation determining section detects that the automatic external defibrillator is activated, is configured to execute an activating process of the lifesaving support apparatus.

The lifesaving support apparatus may further comprise: an activation detecting section which is configured to detect that the automatic external defibrillator is activated. When the determining section determines that the use of the automatic external defibrillator is necessary, the outputting section may continue notification of information for prompting the use of the automatic external defibrillator, until the activation detecting section detects that the automatic external defibrillator is activated.

According to as aspect of the presently disclosed subject matter, a lifesaving support system may comprise: an automatic external defibrillator; a lifesaving support apparatus which is configured to be carried together with the automatic external defibrillator; and a box which is configured to house the automatic external defibrillator and the lifesaving support apparatus. The lifesaving support apparatus may include: a sensor section which is adapted to be attachable to a patient, and which is configured to acquire information of blood flow of the patient; a determining section which, based on the information of blood flow, is configured to determine whether or not a use of the automatic external defibrillator is necessary; an outputting section which is configured to notify a rescuer of information which is determined by the determining section; a carrying-out detecting section which is configured to detect that the lifesaving support apparatus is carried out from the box; and a controlling section which, when the detecting section detects that the lifesaving support apparatus is carried out from the box, is configured to execute an activating process of the lifesaving support apparatus.

According to as aspect of the presently disclosed subject matter, a lifesaving support system may comprise: an automatic external defibrillator; and a lifesaving support apparatus which is configured to be carried together with the automatic external defibrillator. The lifesaving support apparatus may include: a sensor section which is adapted to be attachable to a patient, and which is configured to acquire information of blood flow of the patient; a determining section which, based on the information of blood flow, is configured to determine whether or not a use of the automatic external defibrillator is necessary; an outputting section which is configured to notify a rescuer of information which is determined by the determining section; an activation detecting section which is configured to detect that the automatic external defibrillator is activated; and a controlling section which, when the activation determining section detects that the automatic external defibrillator is activated, is configured to execute an activating process of the lifesaving support apparatus.

DETAILED DESCRIPTION OF EXEMPLARY EMBODIMENTS

Hereinafter, embodiments of the presently disclosed subject matter will be described in detail with reference to the accompanying drawings. In the drawings which are used in the following description, the scale is adequately changed in order to draw components in a recognizable size.

Figure 1:
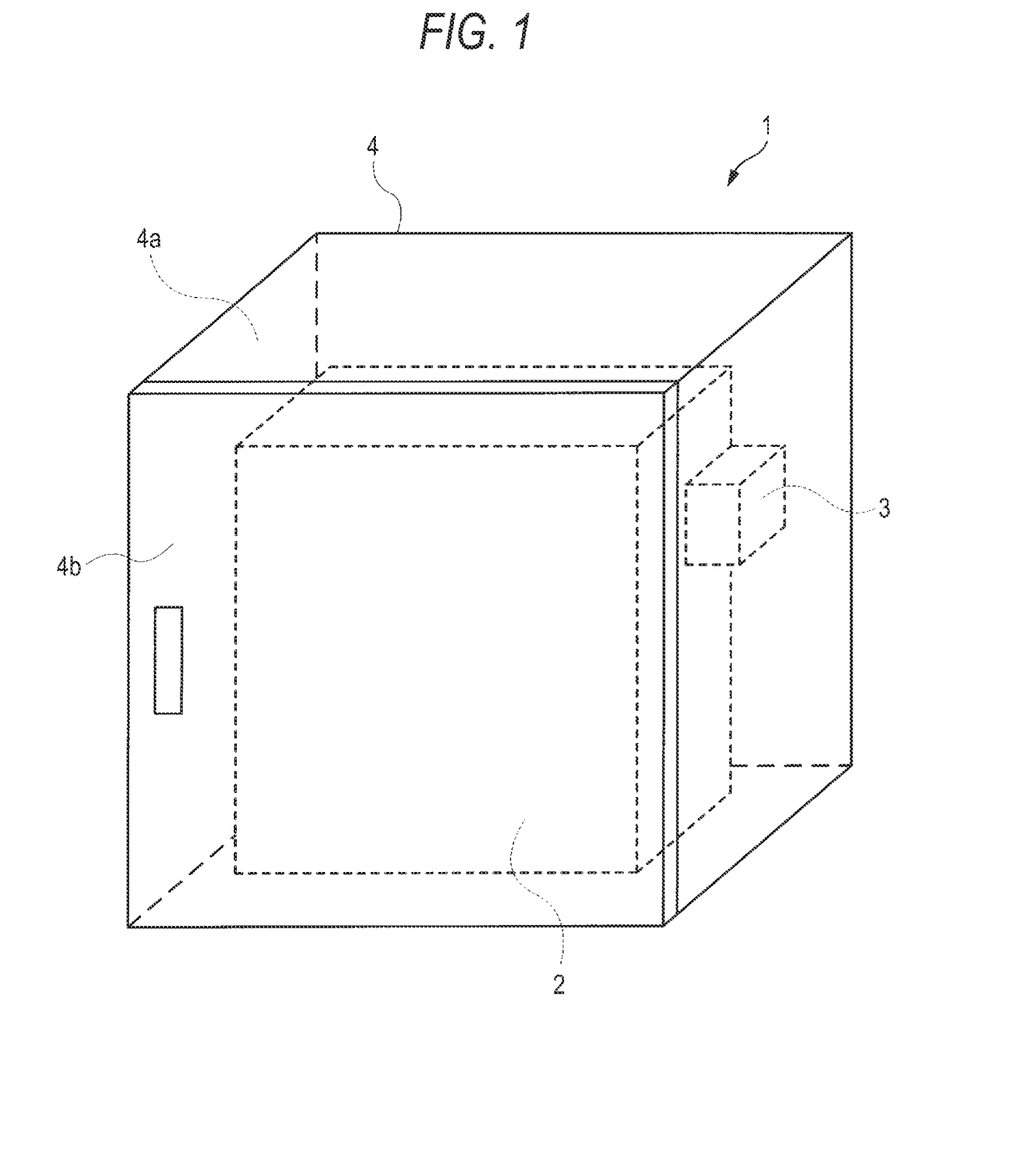
FIG. 1 is a view diagrammatically showing a lifesaving support system of a first embodiment of the presently disclosed subject matter.

FIG. 1 diagrammatically shows a lifesaving support system 1 of a first embodiment of the presently disclosed subject matter. The lifesaving support system 1 is configured by an automatic external defibrillator (hereinafter, abbreviated as AED) 2, a lifesaving support apparatus 3, and a box 4. The AED 2 has a related-art configuration.

The box 4 includes a housing space 4a and a door member 4b which closes the housing space 4a. The box 4 in a state where it houses the AED 2 and the lifesaving support apparatus 3 in the housing space 4a is disposed at a predetermined place. The lifesaving support apparatus 3 is disposed in a state where it can be carried together with the AED 2. When a situation where lifesaving is necessary occurs, the rescuer opens the door member 4b, and carries out the AED 2 and the lifesaving support apparatus 3 from the box 4.

Figure 2:
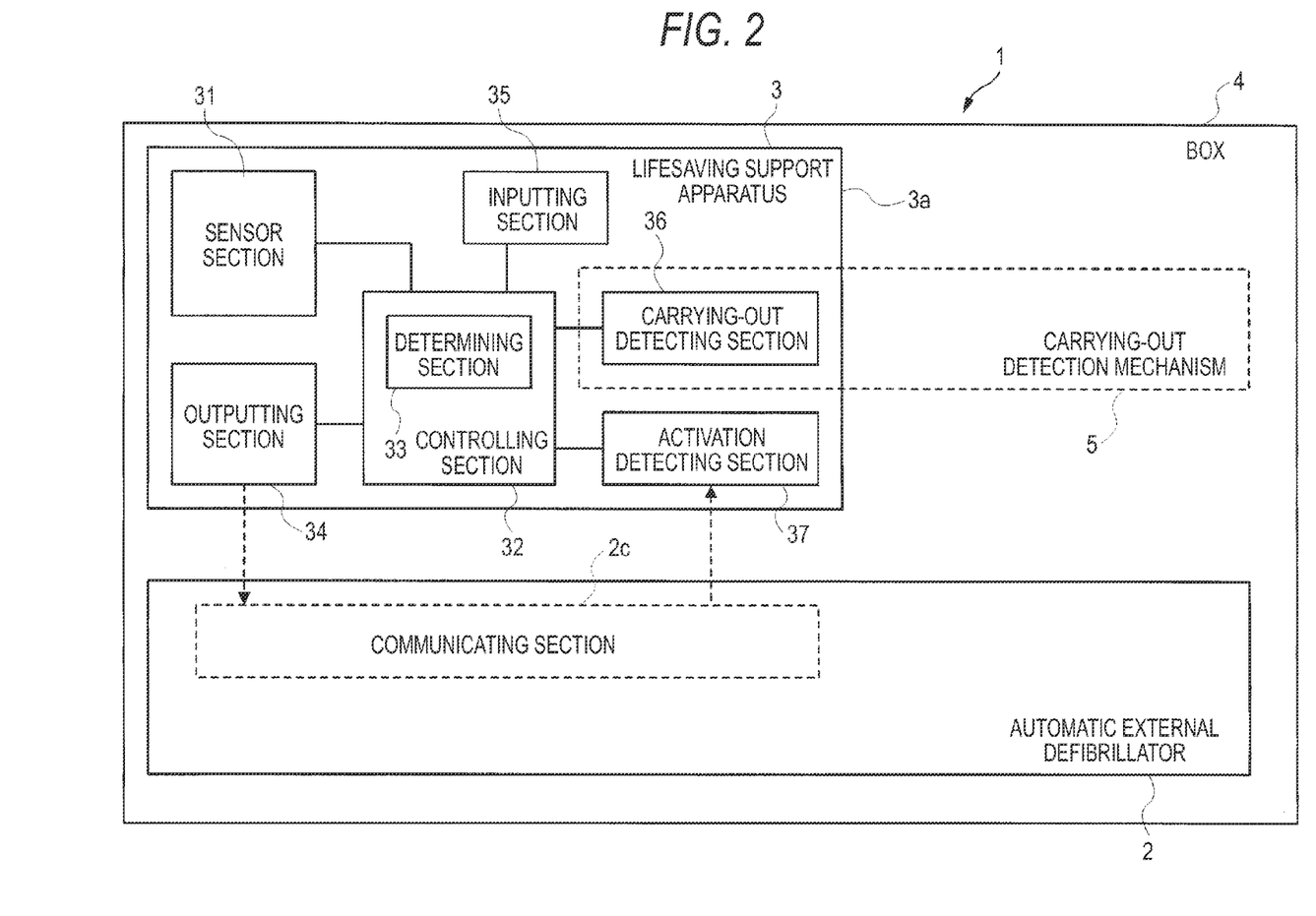
FIG. 2 is a functional block diagram specifically showing the configuration of the lifesaving support system of FIG. 1.
Figure 3:
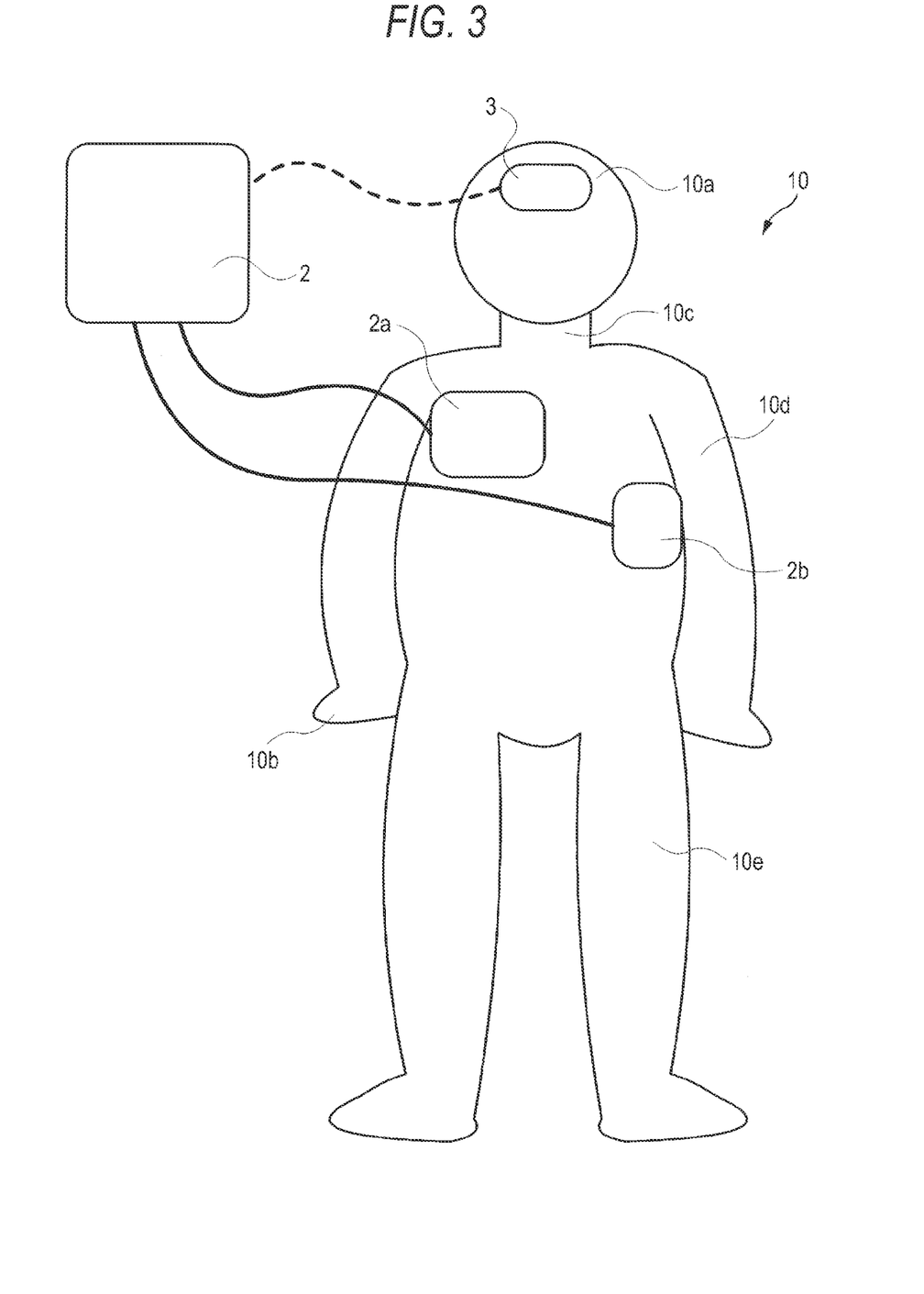
FIG. 3 is a view diagrammatically showing an example of a mode of using an automatic external defibrillator and a lifesaving support apparatus.

FIG. 2 is a functional block diagram specifically showing the configuration of the lifesaving support system 1. The lifesaving support apparatus 3 includes a sensor section 31, a controlling section 32, a determining section 33, an outputting section 34, an inputting section 35, a carrying-out detecting section 36, and an activation detecting section 37. In the embodiment, all of the constituting elements are placed in a single case 3a. As shown in FIG. 3, the lifesaving support apparatus 3 is used while being attached to the forehead 10a of a patient 10. Therefore, the case 3a has a size and shape which allow the case to be attached to the forehead 10a.

The sensor section 31 is configured by a related-art pulse oximeter which has light-emitting and light-receiving portions (not shown). The light-emitting portion is placed so as to be opposed to the forehead 10a of the patient 10, and emits light of a wavelength within the absorption band of blood. Also the light-receiving portion is placed so as to be opposed to the forehead 10a, and receives reflected or transmitted light which has undergone absorption by blood. The light-receiving portion is configured so as to output a signal corresponding to the intensity of received light.

Namely, the sensor section 31 can detect the presence/absence of the pulse as the information of the blood flow, because of the following reason. When the pulsation of the heart is not stopped, the blood flow exists, and, when the blood flow exists, the thickness of blood is changed in accordance with the pulsation. The degree of light absorption, i.e., the received light intensity is changed with the change of the thickness of blood.

The controlling section 32 includes a CPU which executes various calculation processes, a ROM which stores various control programs, a RAM which is used as a work area for data storage and program execution, and the like, and controls the components of the lifesaving support apparatus 3.

The determining section 33 is one of functional blocks which are realized by the controlling section 32. Based on the presence/absence of the pulse which is detected by the sensor section 31, the determining section 33 determines whether it is necessary or not to use the AED 2.

As described above, there are various causes of loss of consciousness of a patient. In some cases, application of an electric shock by the AED 2 is not necessary. In case of cardiac loss of consciousness, application of an electric shock is necessary. This can be determined by the fact that there is no pulse. In case of loss of consciousness due to a brain disorder, copious bleeding, hypoglycemia, anemia, hypocapnia, and the like, application of an electric shock is not necessary (the application should not be performed). This can be determined by the fact that there is a pulse.

Therefore, the determining section 33 is configured so that, when the sensor section 31 detects the fact that there is no pulse, it is determined that the use of the AED 2 is necessary, and, when the sensor section 31 detects the fact that there is a pulse, it is determined that the use of the AED 2 is not necessary.

The outputting section 34 notifies the rescuer of necessity/unnecessity of the use of the AED 2 which is determined by the determining section 33. The notification may be performed in various manners by using at least one of auditory notification (a guidance message, a melody, a beep sound, etc.) and visual notification (lighting of an LED, an indication of a message on a display device, etc.).

The inputting section 35 is configured so that various instructions including the start of the detecting operation by the sensor section 31 can be input. In accordance with the instructions from the rescuer which are input through the inputting section 35, the controlling section 32 controls the components of the lifesaving support apparatus 3.

The carrying-out detecting section 36 detects carrying out of the lifesaving support apparatus 3 from the box 4. Specifically, the carrying-out detecting section 36 includes a vibration sensor which detects vibrations generated when the lifesaving support apparatus 3 is carried out together with the AED 2 from the box 4. When the carrying-out detecting section 36 detects the fact of the carrying out, the controlling section 32 performs an activating process of the lifesaving support apparatus 3. At this time, for example, a guide voice "Attach the sensor to the forehead." is output.

The activation detecting section 37 detects that the AED corresponding to the lifesaving support apparatus 3 is activated. Specifically, the activation detecting section 37 includes an antenna for detecting an electromagnetic wave which is generated by activating the AED 2. When the determining section 33 determines that the use of the AED 2 is necessary, the controlling section 32 continues an announcement for prompting the use of the AED 2 through the outputting section 34, until the activation detecting section 37 detects the fact of the activation. At this time, for example, a guide voice "Activate the AED, and follows its instructions." is output.

When a situation where lifesaving is necessary occurs, the rescuer opens the door member 4b of the box 4 which is disposed at the predetermined place, and carries out the AED 2 and the lifesaving support apparatus 3 from the housing space 4a. The lifesaving support apparatus 3 is activated by vibrations generated at this time. As soon as the rescuer arrives at the place where the patient lies down, therefore, the lifesaving support apparatus 2 can be used. The configuration where the life-saving procedure can be started as quickly as possible contributes to the improved lifesaving rate.

As shown in FIG. 3, the rescuer attaches the lifesaving support apparatus 3 to the forehead 10a of the patient 10, and then operates the inputting section 35 to instruct the start of the pulse detecting process by the sensor section 31. The sensor section 31 detects the presence/absence of the blood flow (the presence/absence of the change of the thickness of blood) by means of the presence/absence of the change of the intensity of light received by the light-receiving portion. The determining section 33 determines whether the use of the AED is necessary or not, in accordance with the detected presence/absence of the pulse.

The result of the determination is notified to the rescuer through the outputting section 34. If no pulse is detected, for example, a guide voice "The pulse is not detected. Use the AED." is output, or at least a part of the display device emits green light. If the pulse is detected, a guide voice "The pulse is detected. Do not use the AED." is output, or at least a part of the display device emits red light.

The lifesaving support apparatus 3 of the embodiment includes the pulse oximeter which can detect the pulse while being attached to the forehead 10a the patient 10. When the apparatus is to be used, therefore, it is not necessary to undress the patient 10. Since the forehead 10a is hardly affected by a body motion, moreover, it is possible to correctly detect the presence/absence of the pulse. In the case where the use of the AED 2 is necessary, therefore, it is possible to provide the rescuer with appropriate instructions. By contrast, in the case where the use of the AED 2 is not necessary, it is possible to avoid a situation where the patient 10 is unnecessarily undressed. Therefore, the privacy of the patient 10 can be protected.

The announcement for prompting the use of the AED 2 is continued until the activation detecting section 37 detects that the rescuer activates the AED 2. Therefore, it is expected to have a function to strongly prompt the rescuer who hesitates to use the AED, to use the AED. Moreover, the certainty of the lead up to the use of the AED 2 can be improved by, for example, replacing the rescuer with another rescuer who can use an AED.

When the activation of the AED 2 is detected by the activation detecting section 37, the controlling section 32 stops the announcement which has been performed through the outputting section 34. In accordance with guide voices output by the AED 2, then, the rescuer attaches electrode pads 2a, 2b to the chest of the denuded patient 10 as shown in FIG. 3, and applies an electric shock to the patient 10 as required.

The outputting section 34 of the lifesaving support apparatus 3 is configured so that, when predetermined instructions are given through the inputting section 35 as required, the information of the blood flow which is acquired by the sensor section 31, i.e., the results of the detections of the presence/absence of the pulse and the arterial oxygen saturation can be output. When the information is output after application of an electric shock, for example, the rescuer can know how the condition of the patient 10 is changed.

The lifesaving support system 1 of the embodiment can be configured without applying any change to the existing AED 2 and box 4. Namely, the AED 2 which has been already disposed is not required to be replaced with a new one, and it is requested only to dispose the lifesaving support apparatus 3 in a manner that it can be carried together with the AED 2. According to the configuration, the lifesaving support system 1 in which the hesitation of the rescuer to use the AED 2 can be suppressed, and the lifesaving rate can be improved can be configured at a minimum additional cost.

Next, a lifesaving support system 1A of a second embodiment of the presently disclosed subject matter will be described with reference to FIG. 4. The configurations which are substantially identical with or similar to those of the first embodiment are denoted by the same reference numerals, and repetitive descriptions are omitted. The lifesaving support system 1A of the embodiment is different from the lifesaving support system 1 of the first embodiment in that a lifesaving support apparatus 3A does not include the carrying-out detecting section 36.

A controlling section 32A of the lifesaving support apparatus 3A of the embodiment is configured so that, when the activation detecting section 37 detects that the AED 2 corresponding to the lifesaving support apparatus 3A is activated, executes an activating process of the lifesaving support apparatus 3A.

As soon as the rescuer carries the AED 2 to the place where the patient lies down, usually, the rescuer first activates the AED 2. Therefore, it is possible to provide the lifesaving support apparatus 3A in which, without delaying the start of the life-saving procedure, the configuration relating to the carrying-out detecting section 36 is omitted, and the production cost is further reduced. Moreover, the lifesaving support system 1A can be configured by using only the AED 2 and the lifesaving support apparatus 3A, and not by using the box 4.

The embodiments have been described in order to facilitate understanding of the presently disclosed subject matter, and are not intended to limit the presently disclosed subject matter. It is a matter of course that the presently disclosed subject matter may be changed or improved without departing the spirit thereof, and includes equivalents thereof.

The place to which the sensor section 31 is to be attached is not limited to the forehead 10a of the patient 10. A configuration where a transmissive type pulse oximeter is attached to the fingertip 10b may be employed. Also in this case, the pulse detecting process can be executed without undressing the patient 10.

The sensor section 31 is not limited to a pulse oximeter. As far as the sensor section 31 can acquire information of the blood flow, the section may be configured as apart of a measuring instrument (such as an ultrasonic blood flow meter, an electromagnetic blood flow meter, a laser blood flow meter, or a Doppler blood flow meter) which uses any one of an ultrasonic wave, an electromagnetic wave, and a laser beam. In this case, the sensor section 31 is attached to the neck 10c, arm 10d, or leg 10e of the patient 10. In any case, the pulse detecting process can be executed while suppressing the degree of undressing of the patient 10 to the minimum.

The sensor section 31 is not limited to have the configuration where the whole section is housed in the case 3a of the lifesaving support apparatus 3(3A). Alternatively, a configuration may be employed where at least a portion which is to be attached to the skin of the patient is disposed outside the case 3a, and a signal indicating the state of the blood flow is supplied to the controlling section 32 through wired or wireless communication.

The carrying-out detecting section 36 is not limited to a vibration sensor. Alternatively, the section may include an acceleration sensor. Also in the alternative, similar effects are attained. As indicated by the broken line in FIG. 2, for example, a carrying-out detecting mechanism 5 in which the state is changed in accordance with the carrying out of the AED 2 and the lifesaving support apparatus 3 may be disposed. As an example of the carrying-out detecting mechanism 5, a configuration may be employed where a magnet is disposed in the box 4, the carrying-out detecting section 36 is configured by a magnetic sensor, and, when the lifesaving support apparatus 3 is separated from the magnet, and the magnetic force which is detected by the magnetic sensor becomes smaller than a predetermined value, the carrying out is detected. Another configuration may be employed where a switch mechanism in which an electrical contact is broken or made by separating the lifesaving support apparatus 3 from the box 4 is disposed.

Figure 4:
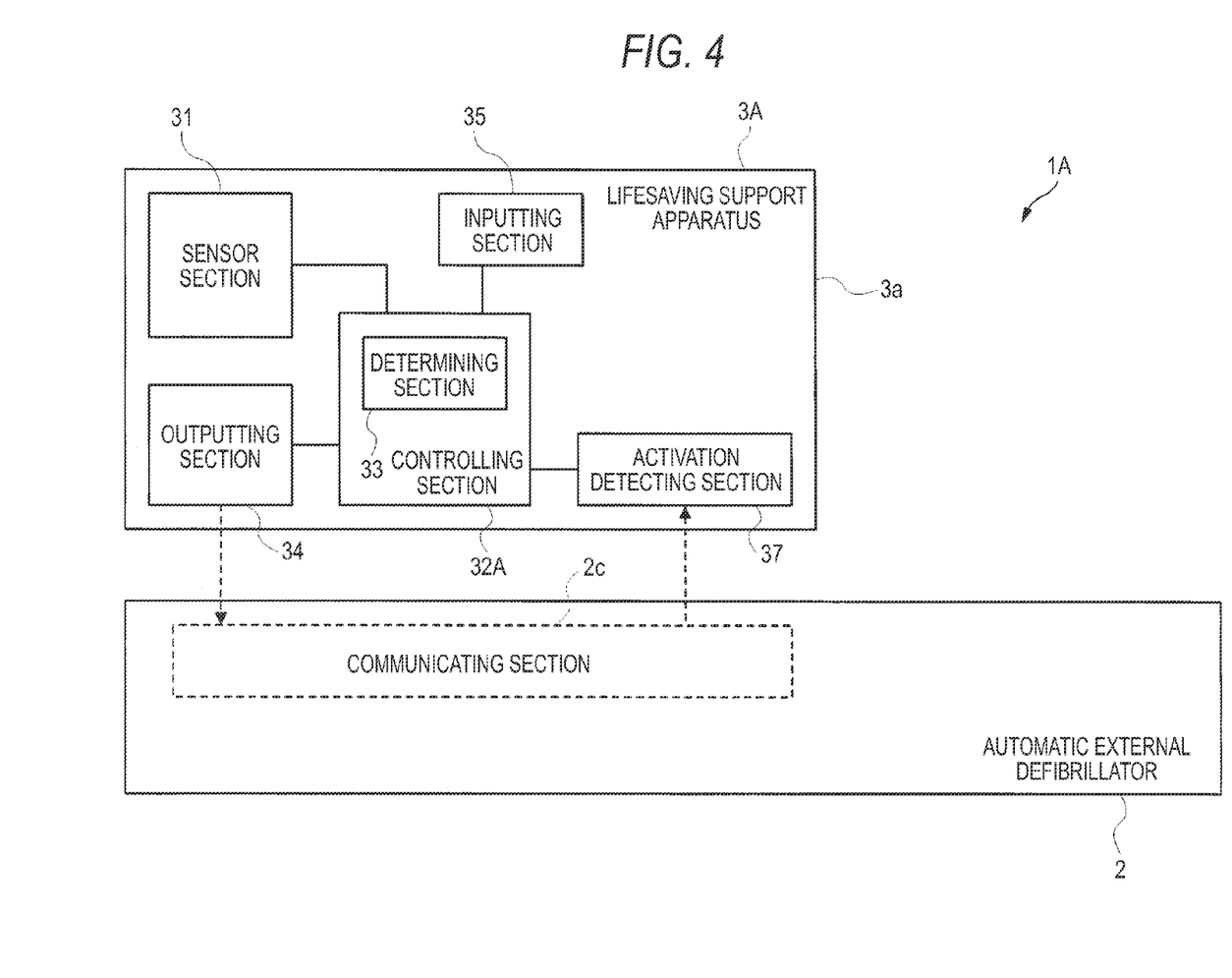
FIG. 4 is a functional block diagram specifically showing the configuration of a lifesaving support system of a second embodiment of the presently disclosed subject matter.

A configuration may be employed where, as indicated by the broken lines in FIGS. 2 to 4, the AED 2 includes a communicating section 2c which can communicate with the lifesaving support apparatus 3(3A) through a wired or wireless connection. In this case, a signal indicating the activation of the AED 2 may be transmitted from the communicating section 2c to the activation detecting section 37, and, when the activation detecting section 37 receives the signal, the controlling section 32(32A) may detect the activation of the AED 2. This enables the process which is to be performed in the lifesaving support apparatus 3(3A) in accordance with the detection of the activation of the AED 2, to be surely performed.

A configuration may be employed where the information of the blood flow which is acquired by the sensor section 31 is transmitted to the AED 2 through the outputting section 34 and the communicating section 2c. In this case, it is possible to configure a system in which the information is reflected in the operation of the AED 2.

The information output from the outputting section 34 is not limited to the information of necessity/unnecessity of the use of the AED 2 which is determined by the determining section 33, and that of the blood flow which is acquired by the sensor section 31. For example, a configuration may be employed where, if it is determined that the use of the AED 2 is not necessary, a voice guiding for procedures to be performed before arrival of a medical person is output, or questions required to know the condition of the patient 10 are made to perform a simple interview.

According to an aspect of the presently disclosed subject matter, a rescuer who is afraid of using an automatic external defibrillator can be provided with appropriate information about whether it is necessary to use the AED or not, thereby supporting the life-saving procedure. In the case where it is determined that the AED must be immediately used, particularly, it is possible to strongly prompt the rescuer to use the AED. By contrast, in the case where the use is determined not to be necessary, it is possible to avoid a situation where the patient is unnecessarily undressed. Therefore, the privacy of the patient can be protected.

According to an aspect of the presently disclosed subject matter, the above-described sensor section can be attached to the forehead, fingertip, neck, arm, or leg of the patient. Therefore, information of the blood flow can be acquired while suppressing the degree of undressing of the patient to the minimum. In the case where the pulse oximeter is attached to the forehead of the patient which is hardly affected by a body motion, particularly, the certainty of acquisition of information of the blood flow can be improved while using a simple configuration.

According to an aspect of the presently disclosed subject matter, since the outputting section is configured to output the information of blood flow which is acquired by the sensor section, after application of an electric shock, for example, the information is output, thereby enabling the rescuer to know how the condition of the patient is changed.

According to an aspect of the presently disclosed subject matter, since the outputting section is configured to output the information of blood flow to the automatic external defibrillator, it is possible to construct a system in which the information is reflected in the operation of the automatic external defibrillator.

According to an aspect of the presently disclosed subject matter, since the lifesaving support apparatus includes a carrying-out detecting section which is configured to detect carrying out of the lifesaving support apparatus from a box in which the lifesaving support apparatus is housed together with the automatic external defibrillator, and a controlling section which, when the detecting section detects the carrying out, is configured to execute an activating process of the lifesaving support apparatus, upon the carrying out of the lifesaving support apparatus from the box, the lifesaving support apparatus is activated. As soon as the rescuer arrives at the place where the patient lies down, therefore, the lifesaving support apparatus can be used. The configuration where the life-saving procedure can be started as quickly as possible contributes to the improved lifesaving rate.

According to an aspect of the presently disclosed subject matter, the lifesaving support apparatus includes an activation detecting section which is configured to detect that the automatic external defibrillator is activated, and when the determining section determines that the use of the automatic external defibrillator is necessary, the outputting section continues notification of information for prompting the use of the automatic external defibrillator, until the activation detecting section detects that the automatic external defibrillator is activated, it is expected to have a function to strongly prompt the rescuer who hesitates to use the AED, to use the AED. Moreover, the certainty of the lead up to the use of the automatic external defibrillator can be improved by, for example, replacing the rescuer with another rescuer who can use an AED.

According to an aspect of the presently disclosed subject matter, since the lifesaving support apparatus includes an activation detecting section which is configured to detect that the automatic external defibrillator is activated, and a controlling section which, when the activation determining section detects that the automatic external defibrillator is activated, is configured to execute an activating process of the lifesaving support apparatus, as soon as the automatic external defibrillator arrives at the place where the patient lies down, usually, the rescuer first activates the automatic external defibrillator. Therefore, it is possible to provide a lifesaving support apparatus in which, without delaying the start of the life-saving procedure, a configuration for detecting the carrying out can be omitted, and the production cost can be further reduced.

What is claimed is:

1. A lifesaving support apparatus adapted to be separately provided from and operably connectable to an automatic external defibrillator, the lifesaving support apparatus comprising:
    a sensor section adapted to be attachable to a patient, and which is configured to acquire information of blood flow of the patient;
    a determining section which, based on the information of blood flow, is configured to determine whether or not a use of the automatic external defibrillator is necessary; and
    an outputting section in operable communication with the determining section which is configured to notify a rescuer of information related to whether or not the use of the automatic external defibrillator is necessary, which is determined by the determining section, wherein,
    when the pulse is absent, the determining section is configured to determine that the use of the automatic external defibrillator is necessary and the outputting section is configured to prompt the rescuer to activate the automatic external defibrillator.

2. The lifesaving support apparatus according to claim 1, wherein the sensor section includes at least a part of a pulse oximeter.

3. The lifesaving support apparatus according to claim 1, wherein the sensor section includes at least a part of a measuring instrument which is configured to use one of an ultrasonic wave, an electromagnetic wave, and a laser beam.

4. The lifesaving support apparatus according to claim 1, wherein the outputting section is configured to output the information of blood flow which is acquired by the sensor section.

5. The lifesaving support apparatus according to claim 4, wherein the outputting section is configured to output the information of blood flow to the automatic external defibrillator.

6. The lifesaving support apparatus according to claim 1, further comprising:
    a carrying-out detecting section in operable communication with the determining section which is configured to detect carrying out of the lifesaving support apparatus from a box in which the lifesaving support apparatus is housed together with the automatic external defibrillator; and
    a controlling section in operable communication with the determining section which, when the detecting section detects the carrying out, is configured to execute an activating process of the lifesaving support apparatus.

7. The lifesaving support apparatus according to claim 1, further comprising:
    an activation detecting section in operable communication with the determining section which is configured to detect that the automatic external defibrillator is activated; and
    a controlling section in operable communication with the determining section which, when the activation determining section detects that the automatic external defibrillator is activated, is configured to execute an activating process of the lifesaving support apparatus.

8. The lifesaving support apparatus according to claim 1, further comprising:
    an activation detecting section in operable communication with the determining section which is configured to detect that the automatic external defibrillator is activated, wherein
    when the determining section determines that the use of the automatic external defibrillator is necessary, the outputting section continues notification of information for prompting the use of the automatic external defibrillator until the activation detecting section detects that the automatic external defibrillator is activated.

9. A lifesaving support system comprising:
    an automatic external defibrillator;
    the lifesaving support apparatus according to claim 1, which is configured to be carried together with the automatic external defibrillator; and
    a box which is configured to house the automatic external defibrillator and the lifesaving support apparatus, wherein
    the lifesaving support apparatus includes:
        a carrying-out detecting section in operable communication with the determining section which is configured to detect that the lifesaving support apparatus is carried out from the box; and
        a controlling section in operable communication with the determining section which, when the detecting section detects that the lifesaving support apparatus is carried out from the box, is configured to execute an activating process of the lifesaving support apparatus.

10. A lifesaving support system comprising:
    an automatic external defibrillator; and
    the lifesaving support apparatus according to claim 1, which is configured to be carried together with the automatic external defibrillator, wherein
    the lifesaving support apparatus includes:
        an activation detecting section which is configured to detect that the automatic external defibrillator is activated; and
        a controlling section which, when the activation determining section detects that the automatic external defibrillator is activated, is configured to execute an activating process of the lifesaving support apparatus.

11. The lifesaving support apparatus according to claim 1, further comprising:
    a case, wherein
    at least the determining section is placed in the case.

12. The lifesaving support apparatus according to claim 1, wherein the outputting section is configured to output a guide voice based on the information determined by the determining section.

* * * * *